(12) United States Patent
Alt

(10) Patent No.: US 6,245,104 B1
(45) Date of Patent: Jun. 12, 2001

(54) METHOD OF FABRICATING A BIOCOMPATIBLE STENT

(75) Inventor: Eckhard Alt, Ottobrunn (DE)

(73) Assignee: Inflow Dynamics Inc., Springfield, VA (US)

(*) Notice: Subject to any disclaimer, the term of this patent is extended or adjusted under 35 U.S.C. 154(b) by 0 days.

(21) Appl. No.: 09/259,906

(22) Filed: Feb. 28, 1999

(51) Int. Cl.⁷ ........................................................ A61F 2/06
(52) U.S. Cl. ........................ 623/1.46; 427/2.24; 623/901
(58) Field of Search .................. 623/1.42, 1.43, 623/1.44, 1.45, 1.48, 901, 1.46; 427/2.24

(56) References Cited

U.S. PATENT DOCUMENTS

| | | | | |
|---|---|---|---|---|
| 4,913,973 | * | 4/1990 | Geusic | 428/469 |
| 5,294,317 | * | 3/1994 | Saito et al. | 204/290 |
| 5,954,761 | * | 9/1999 | Machek et al. | 607/126 |
| 5,980,566 | * | 11/1999 | Alt et al. | 623/1 |

* cited by examiner

Primary Examiner—Cary E. O'Connor

(57) ABSTRACT

A method of forming an iridium oxide coating on a metal stent to achieve a firm attachment of a thin biocompatible coating of the iridium oxide such that the iridium oxide resists being dislodged from the stent upon expansion thereof in a vessel of the human body during implantation of the stent. The method includes submerging the stent in a coating solution having an adequate concentration of iridium chloride in a suitable liquid vehicle, and subjecting the coating solution with stent immersed therein to combined heating and application of ultrasonic energy at a temperature and energy level and for a time interval sufficient to form a coating of iridium oxide of desired thickness and surface roughness on the underlying metal surface of the stent. An biomedical implant with such underlying metal surface of primarily passive structure and an iridium oxide coating as a biologically active surface firmly attached to the underlying metal surface has catalytic properties similar to the normal catalytic activity in the cell cycle of a human body to assist in reducing inflammation associated with contact of the biomedical implant with tissue and blood of the body.

9 Claims, 1 Drawing Sheet

METHOD OF FABRICATING A BIOCOMPATIBLE STENT

BACKGROUND OF THE INVENTION

The present invention relates generally to stents which are implantable or deployable in a vascular or endoluminal location within the body of a patient to maintain the lumen open at that location, and more particularly to improvements in stent coatings for biocompatibility and in methods for applying such coatings.

Stents are expandable prostheses employed to maintain narrow vascular and endoluminal ducts or tracts of the human body open and unoccluded, such as a portion of the lumen of a coronary artery after dilatation of the artery by balloon angioplasty. While vascular usage is frequently discussed in this application, it will be understood by those skilled in the art that stents having the characteristics and features of the present invention may be implanted in other ducts or tracts of the human body to keep the lumen open, such as in the tracheo-bronchial system, the binary hepatic system, the esophageal bowel system, and the urinary tract system.

In the case of an occluded coronary artery, for example, the original blockage is typically attributable to fatty deposits or plaque on the inner lining of the vessel. A different mechanism, however, produces a new blockage after an angioplasty procedure is performed to compress the deposits against the inner lining of the vessel, as by use of balloon angioplasty, or to virtual entirely remove the deposits, as by use of laser angioplasty or rotational cutting. The blood vessel wall is subjected to trauma by any of these procedures, which results in hyperplasia of the neointima, i.e., a rapid proliferation of muscle cells in the affected region of the wall, to cause restenosis and re-occlusion of the vessel lumen in a significant percentage of angioplasty patients within a period of from three to six months following the initial procedure.

To avoid this re-occlusion and to maintain the lumen of the vessel open, it is customary procedure to install a stent at the site in the vessel where the angioplasty was performed. The stent is deployed by radial expansion under pressure exerted by the inflating balloon of a balloon catheter on which the stent is mounted, to engage the inner lining or surface of the vessel wall with sufficient resilience to allow some contraction but also to provide a degree of stiffness to resist the natural recoil of the vessel wall following expansion.

The presence of the stent itself in the bloodstream, however, promotes thrombus formation and clotting as blood flows through the vessel. This, too, can result in sufficient blockage of the coronary artery to produce an infarction. Thrombus formation and clotting at the inner lumen of the stent, and fibrosis and restenosis at the site of the vessel wall where the angioplasty was performed and the outer surface of the stent is now engaged, can be significantly reduced by application of appropriate acutely acting drugs in the locality of the stent. In the past, some difficulty has been encountered in providing a stent surface which is suitable for retention of the necessary drug(s) to achieve those purposes.

Additionally, the composition of the stent, or at least its surface material which is exposed to blood, other body fluid, or tissue, is a factor in the patient's tolerance of the stent in the vascular or endoluminal duct. Of course, the stent must have a composition which is biocompatible with the blood, fluids and tissue of the patient's body. But fully five percent of the human population exhibit allergies to chrome, nickel, and even medical grade 316L stainless steel (about 20% nickel)—materials of which stents are commonly composed. Special biomaterial coatings can provide surfaces which are non-allergenic.

Another important consideration in stent selection and usage is its mechanical strength, particularly in applications where the small size of the duct severely limits the physical dimensions of the stent, such as in a coronary artery. The diameter of the stent and the thickness of its wall or wire must be maintained at a minimum, and yet still offer sufficient mechanical strength to resist the natural recoil of the vessel wall following implantation and to keep the lumen of the vessel open. A steel stent having a wall thickness of from 40 to 50 microns (micrometers, $\mu$m) is feasible for use in the coronary artery and with proper design can be highly flexible when crimped on a balloon while providing significant mechanical strength when deployed. But the small diameter and thin wall of such a stent may not provide enough retention force for film attachment when the stent is crimped onto the balloon, particularly if the stent surface is polished as is frequently the case.

Also, a stent of such small dimensions is virtually not visible on X-ray fluoroscopy as it is being implanted in the patient's body, or afterward when the implant site is examined during patient follow-up, because of its low X-ray absorption.

Therefore, the principal aim of the present invention is to provide a method for manufacturing a small diameter stent which has excellent visibility on X-ray fluoroscopy, as well as high retention force when mounted onto a balloon, and excellent biocompatibility with low thrombogenicity when implanted in a vessel.

A related aim is to provide a method of fabricating a stent in which a ceramic-like structure is applied as an outer layer to a base metal, where the two differ in tensile strength and physical characteristics.

Another important aim of the invention is to provide a stent and method of manufacture thereof in which a suitable coating is provided on the exposed surfaces of the stent to measurably reduce tissue irritation. The reduction in tissue irritation also reduces the traumatic response that produces rapid proliferation of the tissue, and hence, impedes the restenosis attributable to that mechanism. The coating improves thrombogenicity and provides a surface region which may be used to carry an additional biodegradable layer impregnated with anti-fibrotic and anti-thrombotic drugs, for example, which are released to avoid responses tending to initiate a reblockage of the vessel in which the stent is implanted, especially the coronary artery.

Still another objective of the present invention is to provide a stent with a special coating that resists occlusion of a blood vessel at the implant site attributable to mechanical stress-induced hyperplasia of the intimal and neointimal region of the vessel wall, and stent-induced clotting and thrombus formation.

Yet another aim of the invention is to provide a stent which has improved radiopacity for X-ray fluoroscopy viewing without increasing the physical dimensions of the stent.

SUMMARY OF THE INVENTION

In co-pending U.S. patent applications Ser. No. 09/059,053 and U.S. Ser. No. 09/175,919 of one of the applicants herein, both of which are assigned to the assignee of the present invention and incorporated by reference herein, stents and methods of manufacture thereof are described in which the basic stent is provided with multi-layer coatings, the outer layer of which is a ceraic-like material of relatively rough surface. Preferably, this outer layer is very thin and is composed of a compound or derivative of certain metals (including some of the noble metals) suitable as biocompatible coverage, such as either iridium oxide or titanium nitrate, most preferably iridium oxide (sometimes referred to herein as "IROX") This layer overlies the entire exposed surface of the stent, and is advantageous to reduce adverse tissue reaction that occurs in response to contact between the stent and the inner lining of the vessel wall at the implant site.

The ceinic-like, metal derivative layer also provides an improved surface for retention of beneficial drugs or other agents having an anti-thrombotic, anti-platelet, anti-inflammatory, or anti-proliferative function, which are conveniently incorporated in a biodegradable carrier that adheres to the outer surface of the stent and disintegrates or decomposes in the presence of blood or other body fluid to release the drugs or agents therefrom. The IROX-mated outward facing surface of the stent preferably is utilized to retain drugs or agents (collectively referred to herein as substances) that suppress inflammation and proliferation of tissue, whereas the IROX-coated inward facing surface of the stent preferably is utilized to retain substances that suppress thrombus formation and clotting. Layering of the drugs themselves may be used to selectively inhibit acute and longer-term reactions. Details of such biodegradable carriers and impregnated substances are more fully described in U.S. Pat. No. 5,788,979 of one of the applicants herein, assigned to the assignee of the present invention. The disclosure of the '979 patent is incorporated by reference herein.

A vascular stent is typically constructed from an elongate biocompatible metal member composed, for example, of 316L stainless steel (medical grade), titanium, Nitinol (nickel-titanium alloy with shape memory characteristics), idium, or other metal, which is configured in an open-ended cylinrical shape (e.g., coil, mesh, undulating single wire filament or perforated tube). For convenience, the portion of the stent between the open ends thereof is referred to herein as its sidewall, regardless of the particular cylindrical shape of the structure, and the sidewall is referred to herein as having openings therethrough even though a coil stent has only one continuous spiral opening in its sidewall and a continuous filament wire may have very large openings in its "sidewall." When mounted on a balloon or other catheter for implantation, the stent is of sufficiently small diameter to be inserted into and to traverse the vascular system or other duct of the patient's body to a preselected site at which the stent is to be deployed, such as within a coronary artery following or coincident with an angioplasty procedure. Deployment is achieved by application of a uniform radial outwardly directed force on the sidewall of the stent to increase its diameter, and thereby expand or open the stent until it is in firm contact or engagement with the inner lining of the vessel wall. Typically the stent is expanded by inflating a balloon on which it is mounted.

The stent should possess sufficient mechanical strength to resist collapse under the natural recoil force exerted by the vessel wall, when the stent is fully deployed. Iridium oxide, titanium nitrate and related metal derivative coatings have structural characteristics of a ceramic material, with different tensile modulus, brittleness and ductility. Such coatings exhibit little flexibility unless deposited or formed in a sufficiently thin layer to resist flaking or peeling from the underlying metal member during expansion of the stent. Even a very thin IROX layer may undergo some fissuring or cracking during deployment of the stent, owing to the very substantial configurational change and related mechanical stress imposed when the stent goes from its initial or crimped diameter in an unexpanded state to a considerably larger diameter in its expanded state. In practice, this change may be from an initial diameter of one mm to an expanded state diameter of 10 mm or more. The advantages of natural resistance to tissue irritation and improved surface characteristics for retention of beneficial substances may be of little or no value unless suitably tight adherence of the outer layer to the underlying material is achieved.

Various coatings have been employed on stents in the past, such as zirconium oxide and zirconium nitride as disclosed in U.S. Pat. No. 5,649,951 to Davidson, and metals from Group VA of the periodic table as disclosed in U.S. Pat. No. 5,607,463 to Schwartz. In general, these coatings have been used to provide tissue compatibility and/or thrombogenicity, but fail to offer the many additional advantages of iridium oxide.

In the aforementioned '919 application, a muti-layer stent is composed of three different layers consisting of a core material, an intermediate corrosion-resistant layer overlying the core material, and a thin ceramic-like metal or derivative thereof outer layer overlying the intermediate layer. In an exemplary embodiment, the core material is medical grade stainless steel, the intermediate layer is gold, and the outer layer is IROX. A tight adherence of each of the intermediate and outer layers to its respective directly underlying material is essential. Such a tightly adherent coating of gold on steel is achieved by techniques described in U.S. Pat. No. 5,824, 045 of one of the applicants herein, assigned to the assignee of the present invention. While in principle, gold is a very soft and ductile metal which is readily adjusted to different configurations, the ceramic-like noble metal derivative outer coating offers a significantly greater challenge to achieving tight adherence and film attachment to its underlying metal, and maintaining that firm attachment despite the mechanical stress that occurs with substantial configurational change during deployment of the stent to its expanded state.

The present invention provides a method of depositing a ceramic-like coating of suitable biocompatible metal or metal derivative such as iridium oxide for example, onto the base or core metal of a stent, and preferably atop an intermediate noble metal (such as gold) layer to achieve a sufficiently firm attachment of a thin biocompatible layer of the iridium oxide as an outer exposed layer, film or coating of relatively roughened surface characteristics on the stent such that the iridium oxide resists being dislodged therefrom upon expansion of the stent in a vessel (whether it be a blood vessel, a duct or tract) of the human body during implantation of the stent. The method includes the steps of submerging the stent at a stage where the intermediate layer has been applied, or even where only the base metal is exposed, in a solution having an adequate concentration of an iridium compound in a suitable liquid vehicle, and subecting the solution with the stet sub merged therein to combined heating and application of ultrasonic energy at a temperature and energy level and for a time interval sufficient to form on the intermediate layer or directly on the base metal a layer of iridium oxide of desired thickness. The iridium oxide layer is formed with a relatively rough outer surface.

Preferably, combined heating to a specific suitable temperature and application of ultrasonic energy is achieved by the mere application of the ultrasonic energy. In any event, that step is ceased when the layer is of the desired thickness, preferably in a range from about 500 nanometers (mm) to about 1 micron ($\mu$m).

Thereafter, the coated stent is removed from the solion, rinsed with water, and dried at room temperature. The dried coated stent is then heated at a temperature and for a time sufficient to convert residual iridium chloride compounds in the formed layer to oxidized iridium to complete the iridium oxide layer.

The thickness and surface roughness of the layer formed in the solution are controlled by variation of each of the ultrasonic energy source, duration of the coating process, iridium compound, liquid vehicle, and concentration of the selected iridium compound in the liquid vehicle A relatively rough outer surface is well-adapted for retention of selected drugs or agents such as the types mentioned above, in indentations, reservoirs or repositories thereof for time release therefrom after the stent is implanted, as a suitable biodegradable carrier in which the drugs are incorporated undergoes disintegration, to assist the stent in maintaining the lumen of the vessel open. A rough outer surface also serves to increase the friction or retention force of the stent when mounted on a balloon for implantation in the vessel of the human body.

Preferably, the iridium compound is iridium chloride, and the liquid vehicle is formed by dissolving the iridium chloride in a suitable volume of a reduced percentage of hydrochloric acid, boiling the result solution to reduce its volume to approximately one-fifth of its original volume, and then restoring the original volume by adding to that reduced volume of the resulting solution a suitable quantity of 100% isopropanol to constitute the prepared solution in which the stent is to be submerged. The prepared solution is best used in the practice of the method within about seven days after preparation thereof, to form the layer of iridium oxide on the intermediate layer (preferred), or the base metal if no intermediate layer is used After the coated stent is removed from the prepared solution, any residual iridium chloride in the formed layer is converted to iridium oxide by heating the coated stent at a temperature and for a period of time sufficient to produce the conversion, preferably at a temperature in excess of 300° C., for a period of about 12 hours.

The method of combined heating and application of ultrasonic energy is preferably carried out by applying the ultrasonic energy to heat a water bath in which is immersed the containment vessel with stent submerged in the prepared solution therein. For example, the ultrasonic energy is applied at an energy level of 320 watts (2×160 watts, as will be explained below) to vibrate the containment vessel at a frequency of about 35 kHz and to heat the water bath of about 3 liters to its boiling point of 100° C. The heat and vibration are maintained with the ultrasonic energy application for a period of about 5 to 6 hours to produce an iridium oxide layer thickness in the preferred range from about 500 nm to about 1 μm.

Accordingly, it is an additional primal aim of the present invention to provide a method of fabricating a stent (or other implantable medical device) which achieves reliably tight adherence and firm attachment of the metal or metal derivative coating to its underlying intermediate layer or base layer despite configurational changes of the type experienced by the stent (or other implantable medical device) during implantation thereof, and which achieves this in a cost-effective way.

Another aspect of the present invention resides in certain surprising characteristics of the ultrasonically-applied iridium oxide coating which to the applicants' knowledge have not previously been observed in coatings applied by other methods. Applicants' research has shown that the iridium oxide in the outer layer of the stent fabricated according to the method of the invention has catalytic properties. In particular, the research and tests conducted by the applicants herein demonstrates that the iridium oxide coating surface acts as a catalyst in a reaction in the body in which hydrogen peroxide is converted into water and oxygen or an oxide. The effect is that a biologically active surface is created by the primarily passive structure of the iridium oxide coating surface, which measurably assists in preventing inflammatory reactions to the implantation of the structure in the body.

BRIEF DESCRIPTION OF THE DRAWINGS

The above and still further aims, objectives, features, aspects and attendant advantages of the present invention will become apparent from the following detailed description of a preferred method of manufacture or fabrication of coating(s) of a stent and embodiment thereof; constituting the best mode presently contemplated of practicing the invention, when taken in conjunction with the accompanying drawings, in which.

DETAILED DESCRIPTION OF PREFERRED METHOD AND EMBODIMENT

Figure 1:
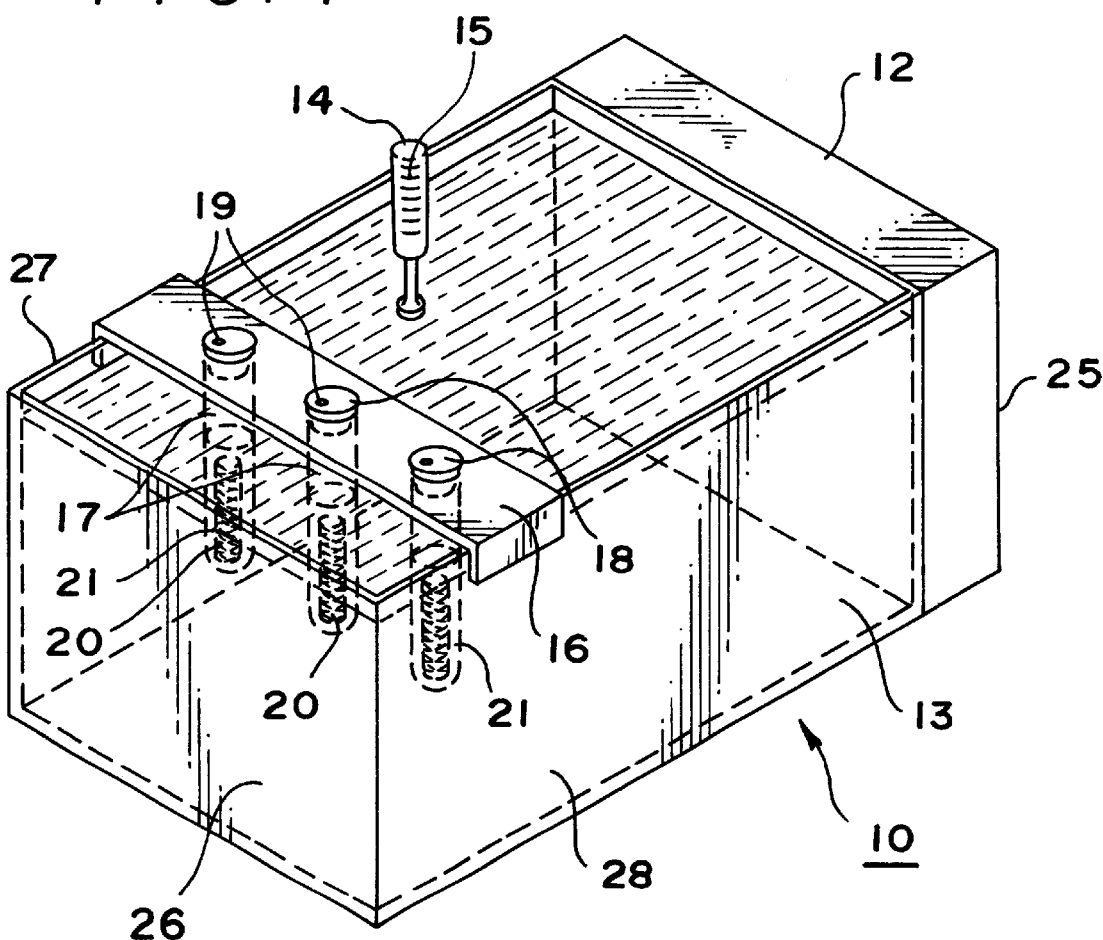
FIG. 1 is a perspective view of an ultrasonic bath with containment vessels for stents in a prepared coating solution, for practicing a preferred method of the invention.

Stents to be coated with a final outer layer of iridium oxide are preferably fabricated initially in the manner disclosed in the co-pending '053 application, but the fabrication of the final layer is instead performed as described herein. Briefly, as described in the '053 application, which is incorporated in its entirety by reference herein, the base metal of the stent which may be medical grade stainless steel, iridium, titanium, Nitinol, or other conventional material used for this purpose, is coated initially with a thin, tightly adherent intermediate layer of noble metal. Preferably the noble metal is gold, or alternatively, an alloy which is primarily composed of gold or other noble metal. This is achieved by a method described in the '045 patent, which is incorporated in its entirety herein by reference. The noble metal layer is applied to cover the entire exposed surface of the base metal stent. For example, this intermediate layer has a thickness in the range from approximately 1 μm to approximately 20 μm, preferably about five μm.

In the preferred process of the '045 patent, gold is deposited onto the surface of the core or base metal of the stent by ion beam deposition to provide a firm, tightly bonded, extremely thin foundation layer, which allows the bond between base metal and noble metal to flex without suffering fracture or peeling of the overlying layer. Gold ions from vaporized gold are accelerated in a vacuum environment to deposit on the exposed surfaces of the metal core of the stent. This initial foundation layer is built upon by then employing a conventional galvanic process to apply one or more additional thin, tightly adherent uniform layers of gold onto the foundation layer to form an over composite layer of gold having a thickness of from about 3 μm to about 6 μm on each side of the sidewall of the stent. Two layers may be applied to the base thickness of the stent wall. The overall effect provides adherence that will inhibit cracking, peeling or flaking of any portion of the overall gold layer from the underlying surface of the steel core, which could otherwise occur during times when the stent is undergoing mechanical stress and distortion, in going from an unexpanded state to and expanded state during deployment.

The thus-far coated stent is then cleaned by heating under vacuum to a temperature that depends on the coating and the underlying material. For gold on steel, for example, the cleaning step may be carried out at a temperature of about 250° C. and a pressure of about 0.10 atmosphere. A final outermost layer of iridium oxide or the like (e.g., titanium nitrate) is then to be formed as a biocompatible layer that serves a primary purpose of avoiding tissue irritation and thrombus formation, with surface roughness for purposes which will be further described below.

A three layer stent structure can be produced with an overall thickness less than or equal to 60 $\mu$m. The stainless steel wall may be fabricated in a thickness of approximately 45 $\mu$m, which offers sufficient mechanical strength to resist the natural recoil of the blood vessel wall following deployment of the stent. The gold intermediate layer is applied in a 5 $\mu$m thickness, for example, to all exposed surfaces of the base layer, giving a total additional thickness of 10 $\mu$m to the structure, and serving to avoid a galvanic potential. The outermost layer of iridium oxide is applied by the method of the invention to a thickness preferably in a range from 500 $\mu$m to about 1.0 $\mu$m.

According to the invention, the method of producing the outermost stent coating of iridium oxide employs a combination of a chemical bath process together with application of heat and mechanical forces. With reference to FIG. 1 of the drawing (not to scale, and for the sake of clarity the bath is shown as being transparent), the preferred environment for performing the coating method includes an ultrasonic bath 10 which has an ultrasonic generator 12 at one end and a container 13 for the water constituting the bath occupying the space between the generator end 25 and the opposite end 26. A thermostat 14 includes an extended thermometer portion which is partly immersed in the water to measure the temperature of the water bath, and a gauge 15 to provide a visual indication of the bath temperature if desired. A damped feedback circuit (not shown) or other conventional means may be coupled to the thermostat and to the ultrasonic generator to maintain the water temperature at the preset level of the thermostat when the ultrasonic bath 10 is in operation.

One or more trays or holders such as 16 are situated for retention at the sides 27 and 28 of container 13, and provided with spaced-apart holes to snugly accept a plurality of substantially identical glass vials 17 therein for partial submergence in the water bath. In the presently preferred embodiment, each of the vials 17 had a liquid content capacity of one milliliter (ml). In practice, the vials or other containers suitable for use in the process of the invention should be sufficiently sized to accept a stent 20 together with sufficient coating solution 21 to cover the stent. In the present example, 500 microliters ($\mu$l) of coating solution is sufficient for that purpose. Each vial 17 is then closed with a stopper or cap 18 to seal the vial except for a tiny hole 19 through the cap to relieve pressure within the vial during operation of the bath in the coating process of the invention.

Using this apparatus (or a similar apparatus as will occur to those skilled in the art from the nature of the preferred coating process), the stent 20 is processed as follows. Before inset the stent into a vial 17, the sure of the stent to be coated with iridium oxide is activated to prepare it for the coating process. For a gold-coated stent, which is preferred, with a base or core metal of medical grade stainless steel, iridium, titanium or Nitinol, for example, adequate surface activation was achieved at this stage of the process by immersing the stent in a 10% solution of oxalic acid at a temperature of about 100° C., for a period of approximately 30 minutes. After "cooling" the stent in this manner, it is rinsed thoroughly with distilled water to remove all traces of the acid. After rinsing, adhesion of water to the activated surface of the stent is prevented by drying the stent in air at a laminar flow at room temperature. At this stage, when fully dried, the stent 20 is inserted into a glass vial 17 for the coating process.

To provide an iridium oxide coating on the stent, a coating solution 21 is first prepared by dissolving 200 milligrams (mg) of iridium chloride in 5 ml of 20% hydrochloric acid, in a separate reaction vial. The resulting solution is then boiled slowly at approximately 100° C. until the solution is evaporated to approximately 20% of its original volume, e.g., from 5 ml to one ml. At that point, the original volume is restored by adding a sufficient quantity of 100% isopropanol. For example, if the original volume of the solution was 5 ml, and it is reduced to one ml by the boiling process, restoration to original volume requires addition of 4 ml of the isopropanol This coating solution may then be stored, but is preferably used within a period of seven days after its preparation.

The coating solution 21 is then added to each glass vial 17 containing a stent 20 so as to fully cover the stent- Am amount of the coating solution required to be added to a vial for a particular stent will depend on and be adjusted according to the size and surface dimensions of the stent to be coated. A stopper 18 is then press-fit into the opening in each vial 17, to prevent evaporation of the liquid contents during operation of the ultrasonic bath 10, and the vials are inserted into separate holes in holder or retention frame 16, which is supported at the sides 27, 28 of container 13 in preparation for further processing of the stents. With this arrangement, the vials 17 are held in an upright position and partially immersed in the bath 10 so that the contents including the stent and coating solution are below or no higher than the surface of the bath liquid. The small opening 19 through the stopper is designed to relieve pressure within the vial during the ultrasonic heating portion of the process.

Since the water level in the bath 10 is at least as high as the level of coating solution 21 in the vials, and the coating solution covers the full height of the stent 20, the entire stent itself will lie completely below the bath water level. Upon commencement of the operation of the bath 10, the ultrasonic generator 12 is activated. In an exemplary laboratory set-up by the applicants herein, a mean energy of 320 watts was delivered by two power heads of 160 watts each, at a frequency of 35 kiloHertz (kHz). This caused the vials 17 and the stents 20 therein to undergo vibration at that same frequency, as well as a heating of the water in bath 10. When the water reaches the boiling point of 100° C., the preset thermostat 14 and associated feedback circuit can maintain the water temperature at that set point value by applying limited flow of coolant water to the exterior of the bath, but in any event the ultrasonic vibrational energy is needed continuously for the adherence of the coating.

Additional water (which may serve a dual purpose of maintaining a set water temperature) may be added to the bath 10 from time to time to compensate for evaporation, or the bath may be held within a separate container to prevent or reduce loss of water by evaporation, or the stent and surrounding coating solution in the vial may be maintained sufficiently below the bath water level to allow for water loss through evaporation without exposing coating solution or stent above the water level during the period of ultrasonic bath operation.

During the overall period of ultrasonic bath operation, by virtue of the ultrasonic vibration and heating the iridium chloride in the coating solution 21 substantially uniformly coats the stent submerged therein with a layer of idium chloride, which is ultimately converted to iridium oxide. Conversion of the iridium chloride to iridium oxide coating takes place during retention of the vials in the bath in the presence of heat and particularly of ultrasonic energy, according to the following reaction:

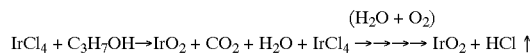

$$IrCl_4 + C_3H_7OH \rightarrow IrO_2 + CO_2 + H_2O + IrCl_4 \rightarrow\rightarrow\rightarrow\rightarrow IrO_2 + HCl \uparrow$$

In the above reaction, iridium tetrachloride ($IrCl_4$) and isopropanol ($C_3H_7OH$) are converted to iridium oxide ($IrO_2$) plus carbon dioxide (CO) plus water $_2(H\ O)$ plus some residual unconverted iridium tetrachloride. But, as will be described immediately below, continued heating at about 320° C. in the presence of air (which includes $H_2O + O_2$) serves to convert the residual $IrCl_4$ into $IrO_2$ and hydrochloric gas (HCl) which evaporates into the ambient atmosphere. Additionally, any molecular bound water in the crystal structure of the iridium oxide leaves the crystal structure following the heating.

After at least 6 hours in the ultrasonically heated water bath 10 at the vapor point temperature, the vials 17 are removed from the bath by withdrawing them from the retention frame 16. The stents 20 are then removed from the vials for post-bath processing. These coated stents are rinsed with de-ionized pure water, and are then dried in a laminar flow of air for approximately one hour at room temperature. Thereafter, the coated stents are placed in an oven and heated for approximately 12 hours at a temperature of 320° C. As noted above, this heating converts any residual iridium chloride which remains in the coating to iridium oxide, so as to create the final complete iridium oxide coating.

Following the latter heating step, the stents are cleaned ultrasonically and with alcohol for about ten minutes, as is customary with biomedical implants.

We found that stents which were on average 16 mm long, with a diameter of 2.0 mm and a strut thickness of 65 ±5 μm underwent an increase in weight in a range from about 0.1 to 0.6 mg, which depended on the desired coating thickness. Thus far, a coating thickness ranging from about 500 nm to about 1 micron has appeared to be optimum.

Tests conducted on stents coated by this method—including vibrational, ultrasonic, bench and maximum expansion/repeated crimping tests—have demonstrated that the iridium oxide is firmly attached to the underlying base or core metal of the stent. Thus, this final outer coating or layer will neither flake off nor disintegrate from the stent even with maximum expansion during subsequent implantation and deployment. The details of these significantly improved performance characteristics of the coating are to be explained by molecular physics. In essence, by the continuous application of ultrasonic energy in the coating method, only those iridium oxide molecules that attach to the underlying base metal enter into a very firm bond, while the other molecules are removed from the stent and, with the ultrasonic induced vibration, are dissolved in the prepared solution.

In further explanation, we have observed that the initial steps of the foregoing process results in a very first layer being formed after surface activation in the presence of oxalic acid ($H_2C_2O_4$). The iridium ($Ir^{4+}$) binds in the presence of the oxalic acid according to the formula:

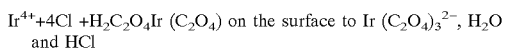

$Ir^{4+} + 4Cl + H_2C_2O_4Ir\ (C_2O_4)$ on the surface to Ir $(C_2O_4)_3^{2-}$, $H_2O$ and HCl This initial binding is very important to the final firm adherence of the outer layer. The additional application of ultrasonic energy in the bath assures that only those molecules which are firmly bound to the surface will attach and form a somewhat rough surface structure. A coating process performed with the same chemical agents but without application of ultrasonic energy forms layers on the surface of iridium oxide that later flake off and break apart when changes are made to the physical dimensions of the stent (or other biomedical implant coated by the same process). Therefore, it is most important that the coating process is done in the presence of ultrasonic energy delivery, which prevents any appositions of the iridium oxide that would subsequently have a tendency to disintegrate or flake off in use. In the ultrasonic bath heating process, an equivalence is reached between apposition and dissolution of the iridium oxide molecules on the surface of the stent.

The thickness of the iridium oxide layer which is formed on the base metal of the stent by virtue of the method of the present invention, as well as the roughness of its exposed surface, are controlled by appropriate variation of the iridium compound, which is iridium chloride in the preferred method, and its amount and concentration in the prepared solution, as well as by the characteristics of the ultrasonic bath. A relatively rough outer surface on the firmly bonded iridium oxide layer, and thus of the overall stent itself provides numerous indentations, reservoirs or repositories for retention of selected beneficial drugs. Desired anti-inflammatory and/or anti-proliferation drugs may be applied to enter these repositories at the rough outward facing surface and adjacent edges of the stent, whereas desired anti-thrombotic and/or anti-platelet agents may be applied to enter the repositories at the rough inward facing surface and adjacent edges of the stent. As a consequence of being stored in this manner, the drugs or agents are, to an extent, time released from the stent to provide a primarily acute response to tissue trauma and clotting mechanisms, and thereby assist in maintaining the lumen of the vessel open.

Additionally, or alternatively, the timed release of the beneficial drugs from these reservoirs in the outer layer surface may be controlled by incorporating the drugs in a biodegradable carrier, preferably of a type disclosed in one of the applicant's U.S. Pat. No. 5,788,979 which is assigned to the assignee of the present invention and incorporated herein in its entirety by reference. Noncontrolled release in this instance is attributable to the speed (including slowness) at which degradation or disintegration of the biodegradable carrier itself occurs, so that the drug or other agent remains captive within the carrier until it is dispensed or released, i-e., freed from its host, by progressive dissolution upon continuing diffusion of the carrier from the reservoir The drug tends to act locally rather than systemically by such an arrangement.

As an alternative to the infusion or incorporation of anti-proliferative or anti-inflammatory drugs into the reservoir along the outward facing porous structure of the outer layer, gene transfer may be used to inhibit the smooth muscle cell growth that leads to neointima and restenosis. In principle, a viral vector is used to transfer the desired information into the genome of the target cells. Viruses capable of such gene transfer are, for example, adenovirus and herpervirus, or fractions of the virus. By viral transfer, which is believed to occur by virtue of absorption and diffusion, part of the genetic information of interest is provided to the target cell. Such information can relate to several mechanisms of cellular proliferation, with the aim of inhibiting restenosis which, if unchecked, could result in at least partial and perhaps complete blockage of the vessel's lumen, despite the presence of the deployed stent at the site.

One important technique involves blocking the proliferation stimulating factors such as cytoKines, nF-kappa B, platelet derived growth factors or other growth factors that originate from platelet deposition, thrombus formation, mechanical stress, or injury and inflammation.

The virus transfer is performed by incorporating the gene transfer agent—a viral vector or virus of the above-mentioned type that contains the viral genetic information desired to be transferred to the target cell(s)—into a biodegradable carrier for release from the reservoir into which it has been infused and dispensed by the process of biodegradation. Alternatively, the release to effect the gene transfer may be accomplished by release from a solution in the reservoir which contains liposomes as the viral vector.

A rough outer surface also serves to increase the friction or retention force of the stent when mounted on a balloon for implantation in the vessel of the human body. A certain risk is present that a balloon catheter-mounted stent might be dislodged from the uninflated or partially inflated balloon as a result of navigation through the tortuous path of the cardiovascular system or other vessels of the body to the preselected site for deployment, particularly if the stent surface is smooth and/or the stent thickness and diameter are small. The rough surface of the outer layer provided by the method of the invention provides the stent with high retention force, exceeding 2.5 Newton, even where less mechanical grip is present because of thin stent strut thickness, and even when the stent is mounted on a small diameter (e.g.,<1 mm) balloon.

According to a farther aspect of the present invention, the stent which has an iridium oxide coating on its base metal is, in essence, an inorganic biomaterial but displays a propensity to reduce the degree of inflammation which otherwise occurs when such a biomaterial is brought into contact with the human body, as by implantation in the body. Normally, an inorganic biomaterial is a passive structure with only passive mechanical properties. But research conducted by the applicants herein has shown that the iridium oxide produced by the method of the invention has catalytic properties, capable of promoting a reaction in which hydrogen peroxide ($H_2O_2$) is converted into water ($H_2O$) and oxygen ($O_2$). This reaction normally occurs only in the presence of a catalyst, since hydrogen peroxide is normally kinetically stable and will not decompose spontaneously. To become unstable, a certain kinetic energy is required to overcome the activation energy for hydrogen peroxide decomposition.

It is known that one of the very first responses of the human body to the implantation of a foreign body, such as a stent surface, into the blood vessels is the activation of leukocytes, white blood cells which are one of the formed elements of the circulating blood system. This activation causes oxidative stress with a burst of reactive oxygen compounds (100 times higher than the baseline production). One of the key molecules in this process is hydrogen peroxide, released by neutrophilic graniocytes which constitute one of the five types of leukocytes. While $O_2$ is always present and generated in a normal cell cycle, in the mitochondria the reaction of $O_2$ to superoxide anion $O_2$ (i.e., reactive form of oxygen when molecular oxygen gains a single electron) is reduced to $H_2O_2$ by the enzyme superoxide dismutase. The enzyme calase serves as a converter of $H_2O_2$. The presence of $H_2O_2$ is a very strong trigger for inflammation. And in a situation where inflammation is occurring, when the granuloytes produce 100 times more $O_2$ than normal, the normal catalytic activity of the body is insufficient to convert the increased amount of $H_2O_2$ to water and oxygen in its metabolic process. But we have discovered that hisi iridium oxide surface of the stent, though a primarily passive structure, is a biologically active surface which is highly effective in preventing inflammatory reactions. This is a surprising discovery of an otherwise biologically inactive surface and of catalytic properties of this biomaterial, which appears to be partly attributable to the nature of the iridium structure owing to molecular adherence as discussed above and partly attributable to the porous sur structure of the iridium oxide layer, to enable the stent to be implanted without significant inflammation even without the use of anti-inflammatory drugs.

It is important to observe that these properties of the iridium oxide coating surface produced by the method of the invention are applicable not only in the specific case of coated stents, but also to other biomedical implants.

Figure 2:
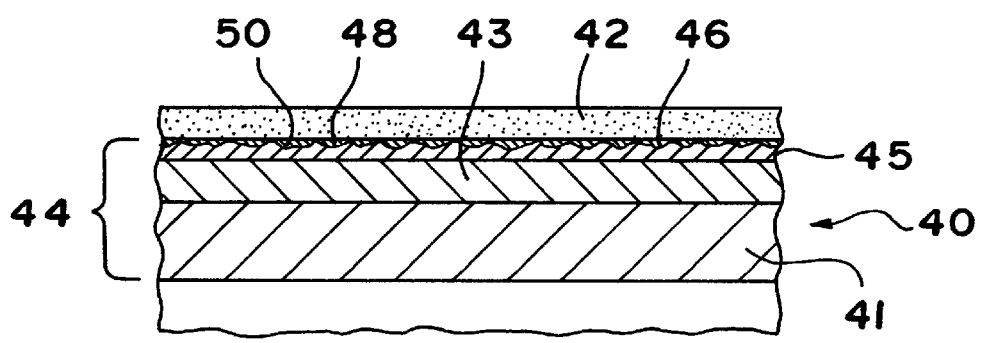
FIG. 2 is a section view of an implantable stent with iridium oxide coating formed by the method of the invention.

With reference to FIG. 2, a metal device, instrument or prosthesis 40 is shown in an exaggerated crossectional view in which it is implanted in a human body at an adjacent layer of tissue 42. For example, the device 40 may be a stent which is implanted in an artery whose wall is illustrated as 42. It will be understood that only a fragmentary portion of the stent is shown in the Figure. The sidewall 44 is composed in part of base metal layer 41, and intermediate gold layer 43 which enhances visibility of the stent and provides a complete coverage of the base metal as an hermetic seal. The outer layer 45 is composed of iridium oxide with a rough outer surface 46. Layer 45 is formed on the intermediate gold layer 43 by the method which has been described with reference to FIG. 1. The repositories or reservoirs 48 formed in the porous surface may be impregnated with a biodegradable carrier 50 into which the appropriate beneficial substances are incorporated.

Although certain preferred and alternative methods and embodiment of the present invention have been disclosed herein, it will be appreciated by those skilled in the art to which the invention pertains, from a consideration of the foregoing description, that variations and modifications may be made without departing from the spirit and scope of the invention. Accordingly, it is intended that the invention shall be limited only by the appended claims and the rules and principles of applicable law.

What is claimed is:

1. A method of forming an iridium oxide coating on a stent to achieve a firm attachment of a thin biocompatible layer of the iridium oxide such that the iridium oxide resists being dislodged upon expansion of the stent in a vessel of the human body during implantation of the stent, said method comprising the steps of submerging the stent in a solution having an adequate concentration of an idium compound in a suitable liquid vehicle, and subjecting said solution with said stent immersed therein to combined heating and application of ultrasonic energy at a temperature and energy level and for a time interval sufficient to form a layer of iridium oxide of desired thickness on said stent.

2. The method of claim 1, wherein said stent includes a biocompatible metal base, and an intermediate unoxidized noble metal layer overlying and adhered to said base, and wherein said iridium oxide layer is formed atop and adherent to said intermediate noble metal layer.

3. The method of claim 1, wherein said iridium compound is iridium chloride, and said combined heating and application of ultrasonic energy is performed by heating a water bath in which a containment vessel with said solution therein is immersed with said ultrasonic energy applying said ultrasonic energy at an energy level of about 320 watts to vibrate said containment vessel at a frequency of about 35 kHz and heat said water bath to its boiling point of 100° C. and maintaining said heat with said ultrasonic energy application for a period of about 5 to 6 hours to produce said iridium oxide layer thickness.

4. The method of claim 3, wherein said layer thickness is a thickness in a range from about 500 nm to about 1 $\mu$m.

5. A method of producing a firm attachment of an iridium oxide coating on an underlying intermediate noble metal layer of different constituency overlying and adherent to a base metal of a biomedical implant, comprising forming said coating on said underlying intermediate noble metal layer in the presence of ultrasonic energy.

6. The method of claim 5, wherein said ultrasonic energy is applied to a bath in which is immersed a containment vessel for a coating solution with said biomedical implant submerged therein, and heat is applied simultaneously with said ultrasonic energy to said bath at a temperature, frequency and energy level and for a period of time sufficient to form said coating of desired thickness on said underlying layer.

7. The method of claim 1, wherein said bath is heated to said temperature by said application of ultrasonic energy thereto.

8. A method of producing a biocompatible outer surface on a stent by forming a surface layer on the stent with firm attachment to an underlying intermediate noble metal layer overlying a biocompatible core metal of the stent, in which said underlying intermediate noble metal layer is softer and more ductile than said surface layer, said method comprising coating said underlying intermediate noble metal layer from a solution for producing said surface layer while applying heat by application of ultrasonic energy to a bath in which said stent and coating solution are contained.

9. The method of claim 8, wherein said surface layer is iridium oxide and said underlying metal surface is gold.

* * * * *